United States Patent
Woessner

[11] Patent Number: 5,919,170
[45] Date of Patent: Jul. 6, 1999

[54] URINARY CATHETER

[75] Inventor: Roger Woessner, St. Paul, Minn.

[73] Assignee: Mentor Corporation, Minneapolis, Minn.

[21] Appl. No.: 08/486,379

[22] Filed: Jun. 7, 1995

Related U.S. Application Data

[63] Continuation-in-part of application No. 08/260,678, Jun. 6, 1994, abandoned, which is a continuation-in-part of application No. 08/012,021, Feb. 1, 1993, abandoned.

[51] Int. Cl.[6] .................................................. A61M 25/00
[52] U.S. Cl. .......................................... 604/264; 604/280
[58] Field of Search ..................................... 604/264, 280, 604/52–54

[56] References Cited

U.S. PATENT DOCUMENTS

| | | | |
|---|---|---|---|
| 2,212,334 | 8/1940 | Wallerich . | |
| 2,857,915 | 10/1958 | Sheridan | 604/280 X |
| 3,086,525 | 4/1963 | Whitcomb | 128/658 |
| 3,190,290 | 6/1965 | Alley . | |
| 3,295,527 | 1/1967 | Alley et al. | 604/280 |
| 3,369,542 | 2/1968 | Thaidigsman | 604/280 X |
| 3,459,189 | 8/1969 | Alley et al. . | |
| 3,568,817 | 3/1971 | Douglas | 198/377 |
| 3,788,328 | 1/1974 | Alley et al. . | |
| 3,903,895 | 9/1975 | Alley et al. . | |
| 4,027,659 | 6/1977 | Slingluff | 604/280 |
| 4,279,252 | 7/1981 | Martin | 128/658 |
| 4,368,023 | 1/1983 | Hannah et al. | 425/392 |
| 4,704,111 | 11/1987 | Moss | 604/280 |
| 5,045,071 | 9/1991 | McCormick et al. | 604/280 |
| 5,360,414 | 11/1994 | Yarger | 604/264 |

FOREIGN PATENT DOCUMENTS 9106255  5/1991  WIPO .

OTHER PUBLICATIONS

Mentor Corporation, Health Care Products, "Self–Cath", Santa Barbara, California (1990).

*Primary Examiner*—Corrine M. McDermott
*Attorney, Agent, or Firm*—Fish & Richardson P.C., P.A.

[57] ABSTRACT

A urinary catheter including a tube with a co-extruded stripe, printed stripe or demarcation or series of marks to determine the alignment of a tip end of the catheter relative to the striped or marked portion of the catheter outside the body. The catheter can be a urethral catheter, such as a Coude-Tiemann curve tip catheter. This visible stripe or marks provide for manipulating passage of the catheter tip through obsructed or difficult urological pathways.

37 Claims, 12 Drawing Sheets

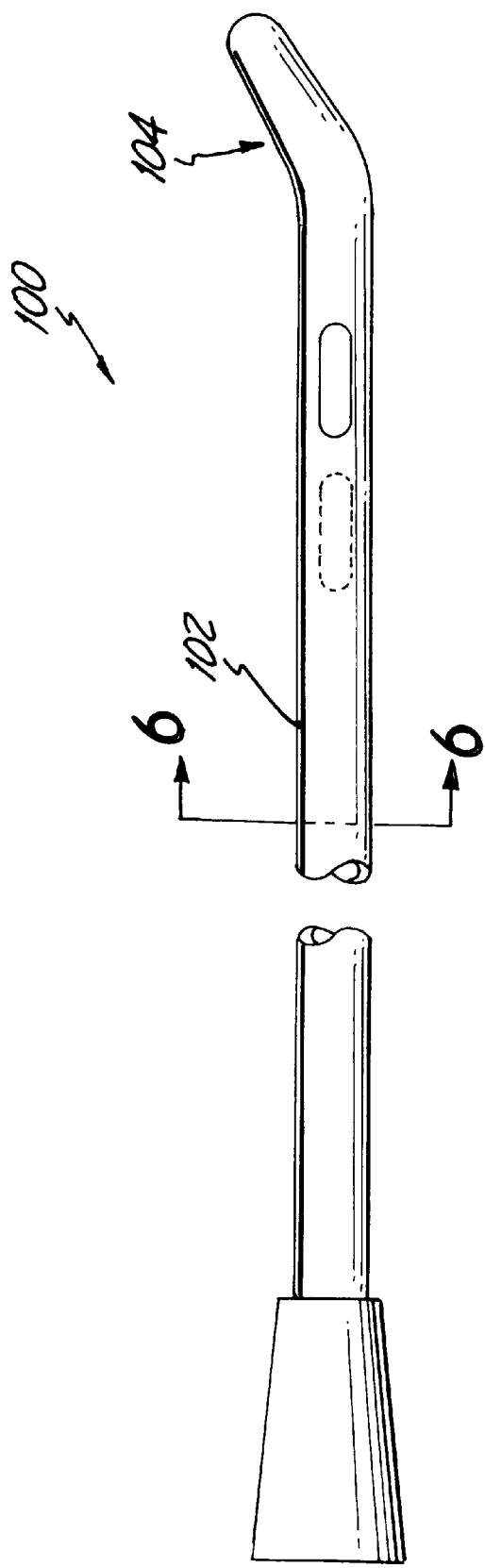

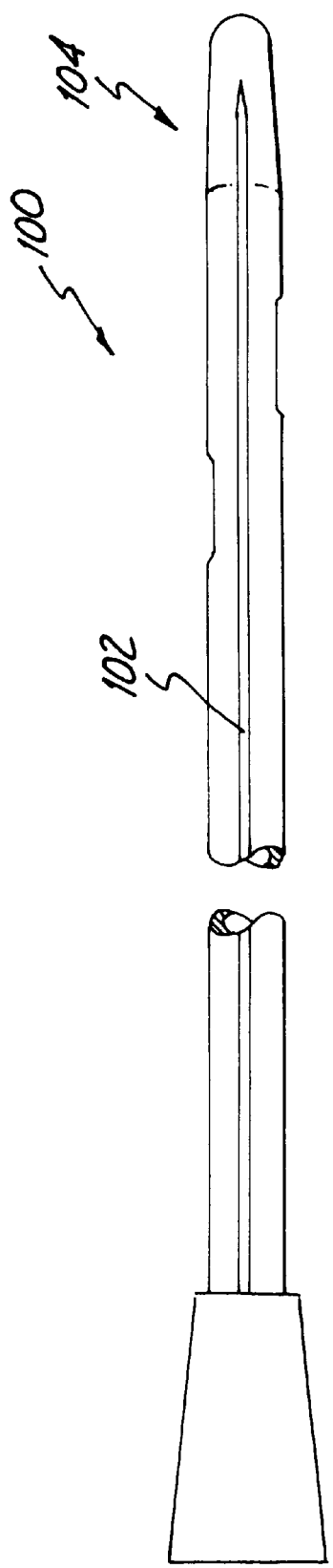

URINARY CATHETER

CROSS REFERENCE TO CO-PENDING APPLICATION

This application is a continuation-in-part of Ser. No. 08/260,678, filed Jun. 6, 1994, now abandoned, which is a continuation-in-part of Ser. No. 08/012,021, filed Feb. 1, 1993, now abandoned, and the benefit of priority under 35 USC §120 is hereby claimed.

BACKGROUND OF THE INVENTION

1. Field of the Invention

The present invention pertains to a catheter, and more importantly, pertains to a catheter with a longitudinal co-extruded stripe or printed stripe or marking or longitudinal sequence of markings, such as for urological catheters.

2. Description of the Prior Art

Prior art catheters have generally been clear, polymer tubing, and it is impossible to tell the alignment of the tip and/or holes of the catheter relative to the portion of the catheter outside the body. If the catheter has been passed down through a particular pathway, such as a urological pathway, withdrawal of the catheter through a passage can cause injury to the tissue of the passage way.

The present invention overcomes the disadvantages of the prior art by providing a catheter with a longitudinal stripe or sequence of markings for illustrating the orientation of the tip end of the catheter relative to the portion outside the body.

SUMMARY OF THE INVENTION

The general purpose of the present invention is to provide a catheter with a longitudinal stripe or longitudinal sequence of markings to indicate the orientation of the tip end and/or holes relative to the striped or marked portion of the catheter outside the body.

According to one embodiment of the present invention, there is provided a catheter including a longitudinal polymer tube, a co-extruded stripe or printed stripe or a demarcation or sequence of markings along the length of the longitudinal polymer tube, a connector on one end and a catheter tip on the other end. The catheter can be a urological catheter. The longitudinal stripe also provides an indication of torque on the catheter.

Significant aspects and features of the present invention include a catheter with a longitudinal stripe or sequence of markings to indicate the orientation of the catheter tip and/or hole location relative to the striped or marked portion of the catheter outside the body, or to indicate the torquing on the catheter.

Another significant aspect and feature of the present invention is a catheter with a longitudinal stripe or sequence of markings where the stripe or marking are co-extruded, printed or marked, which pertains to urological catheters.

A further significant aspect and feature of the present invention is a teaching of utilizing a stripe or sequence of markings on a urological catheter to indicate the orientation of the tip and/or hole(s) with respect to the connector or distal end of the catheter.

Other significant aspects and features of the present invention of the stripe or marks on a catheter is that the stripe or marks provide for the monitoring the orientation of a curved tip. Also the stripe or marks provide for visual monitoring a straight catheter with a rounded tip to indicate the particular and exact orientation of any holes relative to the striped or marked portion of the catheter outside the body. Further, the stripe or marks, whether the catheter is completely closed, provides the exact location of the holes adjacent at the tip end, and the stripe or marks provide for visually monitoring axial rotation of the catheter for precise positioning of the holes. Finally, the stripe or marks on a catheter are an indication of any torquing on a catheter whether the catheter be a closed-end catheter or an open-end catheter. The teachings of the stripe or mark(s) are also applicable and can also be used for bubble-tubing catheters with a flared tip end.

Having thus described embodiments of the present invention, it is an object of the present invention to provide a striped or marked polymer catheter.

One object of the present invention is to provide a catheter with a co-extruded stripe, printed stripe or demarcation or sequence of markings to indicate the orientation of the tip of the catheter and any torquing on the catheter. The stripe or marking(s) also indicate the orientation of the holes in the tip end of the catheter. Teachings of the present invention are also applicable to other medical devices which are longitudinal and inserted into the body.

Another object of the present invention is a urological catheter with a co-extruded stripe, printed stripe or demarcation or sequence of markings through suitable printing or marking processes.

A further object of the present invention is a striped or marked catheter where the stripe or mark(s) provides an indication of the orientation of the tip of the catheter and also the degree of torquing, if any, of the catheter.

Other objects of the present invention of the stripe or mark(s) on a catheter is that the stripe or mark(s) provides for visual monitoring of the orientation of a curved tip. Also the stripe or mark(s) provide(s) that visual monitoring of a straight catheter with a rounded tip indicates the particular and exact orientation of any holes relative to the striped or marked portion of the catheter outside the body. Further, the stripe or mark(s), whether the catheter is completely closed, provides the exact location of the holes adjacent the tip end, and the stripe or mark(s) provides for axial rotation of the catheter for precise positioninq of the holes. Finally, the stripe or mark(s) on a catheter is an indication of any torquing on a catheter whether the catheter be a closed-end catheter or an open-ended catheter.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 4 illustrates a side view of a tapered catheter, an alternative embodiment of the present invention;

FIG. 5 illustrates a top view of FIG. 4;

FIG. 14 illustrates yet another embodiment of the visible sequence of marks in the present invention.

DETAILED DESCRIPTION OF THE PREFERRED EMBODIMENTS

Figure 1:
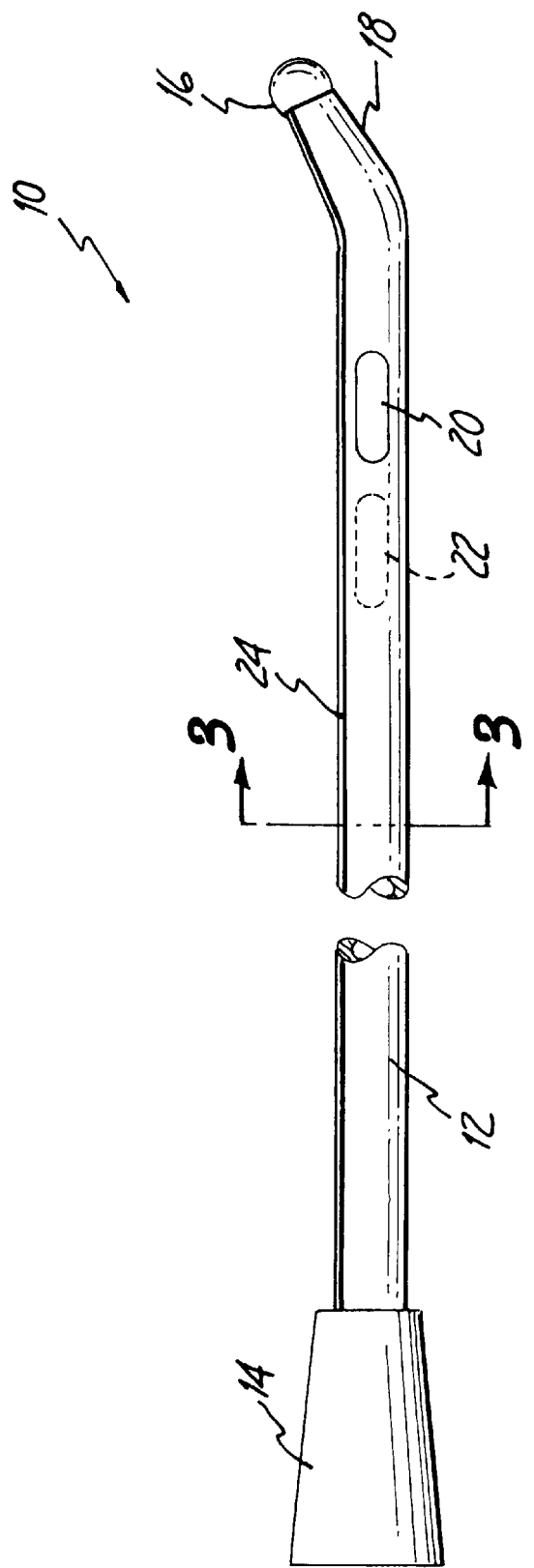
FIG. 1 illustrates a side view of a tapered urinary catheter, the present invention.

FIG. 1 illustrates a catheter 10 including a longitudinal polymer tube 12, a connector 14 welded to the polymer tube 12, and a preformed tip 16, which can assume any geometrical and medical configuration by way of example and for purposes of illustration only and not to be construed as limiting of the present invention. In this particular example, the tip reassembles a Coude/Tiemann curved tip catheter tip 18 with two conforming longitudinal holes 20 and 22. A visible co-extruded stripe, printed stripe, marked stripe or demarcation 24 runs along the longitudinal length of the catheter 10 from the tip 16 to the connector 14. Co-extruding processes are known extruding process. The co-extruding process can provide a colored stripe or mark either in the polymer tube or on the polymer tube. Printing or marking of polymers are known processes.

Figure 2:
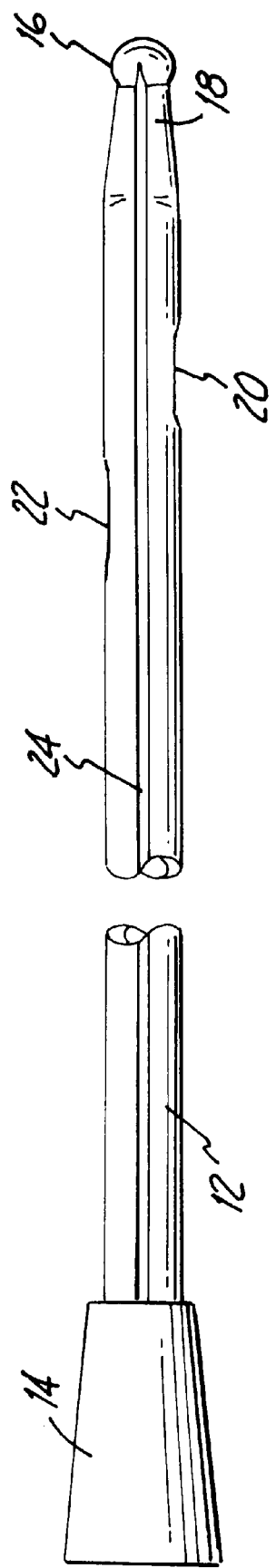
FIG. 2 illustrates a top view of FIG. 1.

FIG. 2 illustrates a top view of FIG. 1 where all numerals correspond to those elements previously described.

Figure 3:
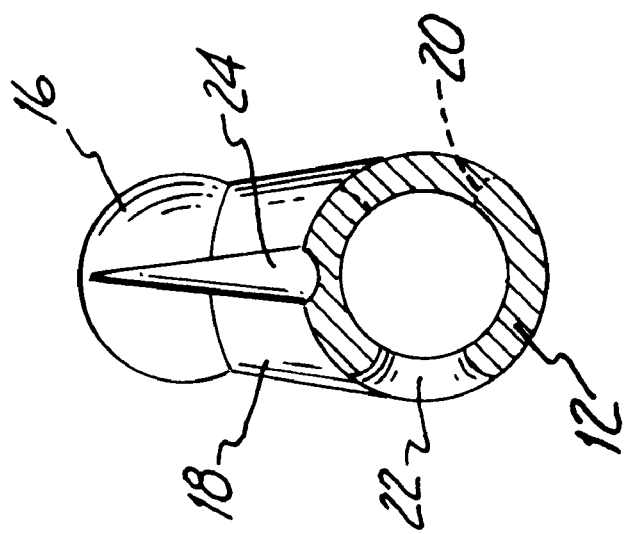
FIG. 3 illustrates a view taken along line 3—3 of FIG. 1.

FIG. 3 illustrates a view taken along line 3—3 of FIG. 1 where all numerals correspond to those elements previously described.

Mode of Operation

The utilization longitudinal striped or marked catheter provides many advantages for executing tortuous urological pathways, especially when the catheter is removed. The visible stripe or marks provides for knowing the orientation of the longitudinal holes relative to the position of the insertion, and also for knowing the position of the tip, especially for Coude-Tiemann curved tip urological catheters. It is especially important for obstructed or difficult urological pathways. The visible stripe or marks also provides for registration, producing closed-tolerance catheters. The visible stripe or marks also provides for displaying the torque or twist effect of the catheter during use.

Description of an Alternative Embodiment

FIG. 4 illustrates a side view of a tapered catheter 100, an alternative embodiment of the present invention with a visible stripe 102 which can be co-extruded, printed or marked in or on the top surface of the catheter to indicate alignment of the tip and/or the holes, and to indicate any torquing. All other structure including the polymer tube, the longitudinal holes, and the connector are structurally the same as for FIGS. 1–3. The only difference is the tip 104. The polymer tube, eyelets or holes and the tip can be any predetermined geometrical configuration. The stripe 102 for the catheter would be either co-extruded into or on the tube. In the alternative, the stripe could be printed or marked or could even be a series of marks. Typically the visible stripe is of contrasting color with the polymer tubing so as to be readily apparent to an operator. On clear polymer tubing, for example, the stripe could be blue in color. The material suitable for the catheter tubing of the present invention is well known in the art of catheterization and plastic medical devices, wherein the suitable polymers are flexible, biocompatible and semi-transparent to opaque in appearance. While not being limited by example, polyurethane, polyvinylchloride, natural or silicone rubbers, Teflon or other transparent thermoplastics could be utilized in the catheter of the present invention.

FIG. 5 illustrates a top view of FIG. 4 where all numerals correspond to those elements previously described.

Figure 6:
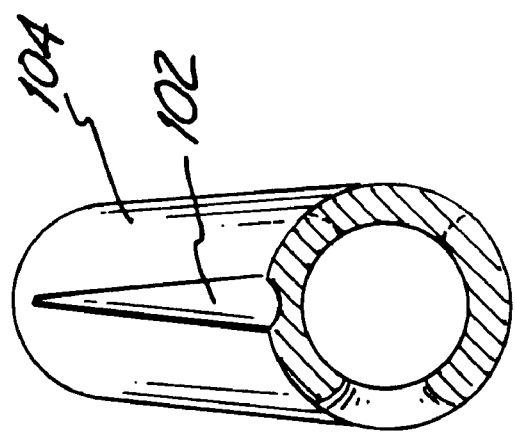
FIG. 6 illustrates a view taken along line 6—6 of FIG. 4.

FIG. 6 illustrates a view taken along line 6—6 of FIG. 4 where all numerals correspond to those elements previously described.

Referring now to FIGS. 7–10, a urinary catheter is shown with an unobstructed insertion and in a variety of obstructed insertion situations. In the preferred embodiment, longitudinal holes 20 and 22 are arranged at 3 and 9 o'clock relative to the catheter tip 16. Applicant has found that these positions for the longitudinal holes cause less trauma to the urinary track upon insertion or removal of the urinary catheter. The visual stripe 24 allows the operator to know where eyelets or holes 20 and 22 and the tip are relative to the portion of the catheter outside the body during the insertion process. Therefore, if during insertion, the operator can feel that the insertion force causes the greatest force and tissue pressure at 12 and 6 o'clock relative to the tip going around a turn, then having the holes at 3 and 9 o'clock will cause the least amount of tissue damage. Without the visual stripe, the operator is unable to determine the position of the holes 20 and 22 as they guide the catheter around a blockage or obstruction.

Figure 7:
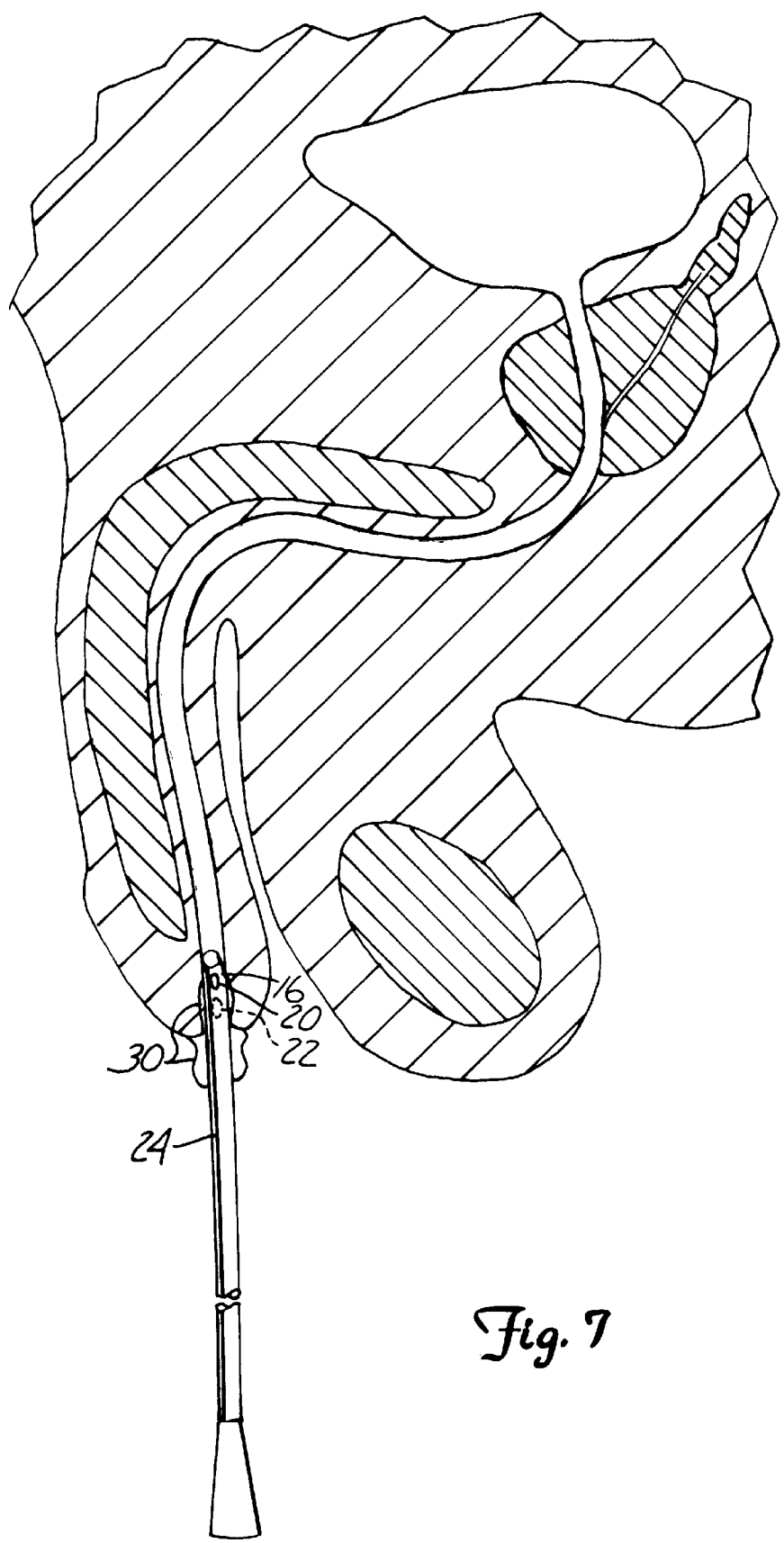
FIG. 7 illustrates a side view of the urinary catheter during an unobstructed insertion.

FIG. 7 shows a side view of the urinary catheter during an unobstructed insertion and shows that stripe 24 is perfectly straight. In FIG. 7, reference numeral 30 indicates lubrication which is well known in the art. Visual stripe 24 can be any desired color, for example blue or black, so long as it provides readily visible contrast to the color of the tube.

Figure 8:
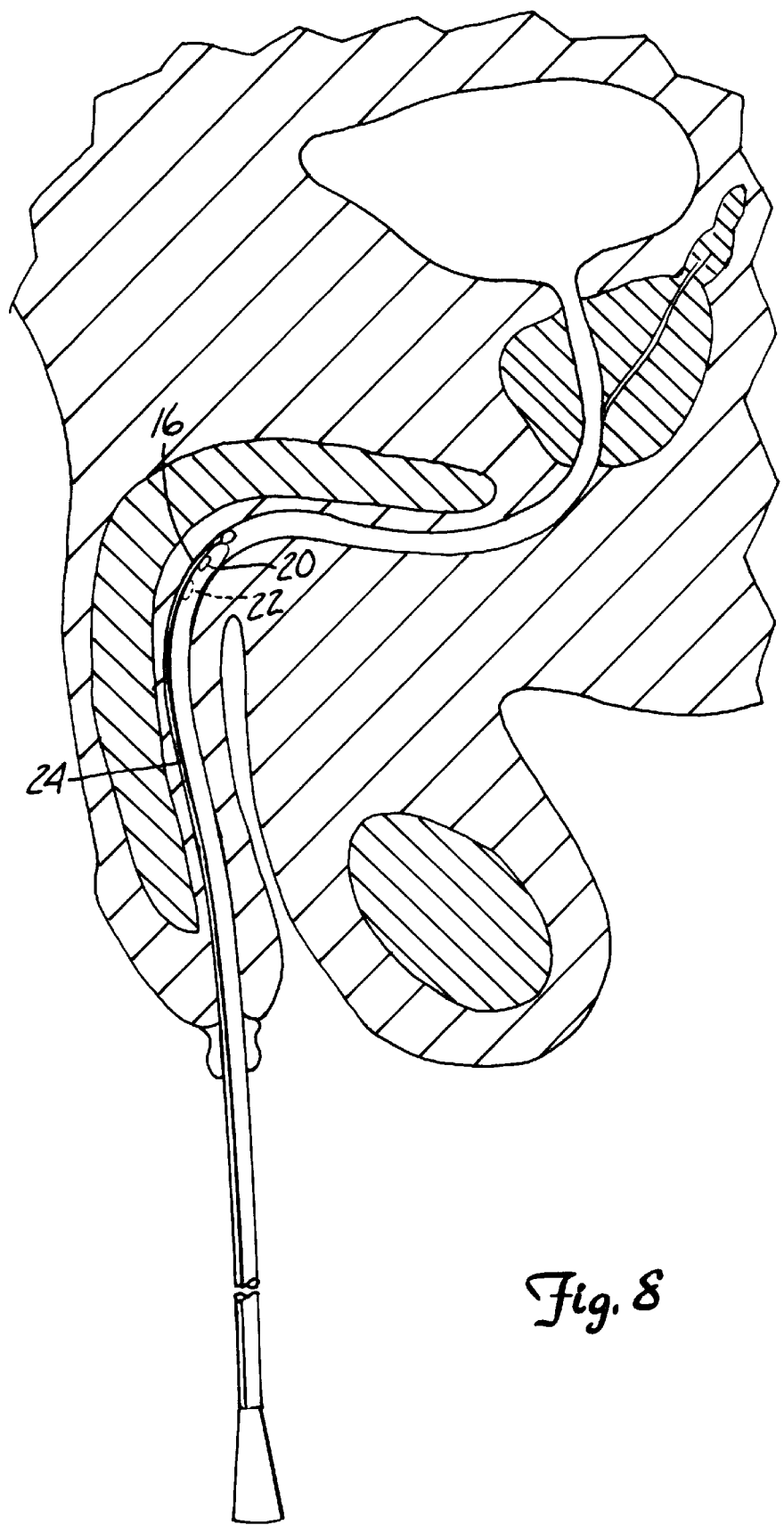
FIG. 8 illustrates a side view of an obstructed insertion showing the visual stripe twisted.

FIG. 8 shows a catheter 10 with the visual stripe 24 twisted. A well known urinary catheter insertion technique uses the so-called one-quarter turn, back and forth, push insertion method. In an unobstructed track, rotation of the catheter does not create this twist, since the entire longitudinal length of the catheter rotates together (see FIG. 7). However, if the catheter encounters a growth, scarring or obstructions in the urinary track, the greater frictional force exerted on tip 16 will prevent the entire axial length of the tube 12 from rotating simultaneously, causing the twisted visual stripe 24 of FIG. 8. To one skilled in the art, the visual stripe of FIG. 8 provides a great deal of information about the obstruction encountered by the catheter tip 16. All prior art catheters of which Applicant is aware utilize clear tubing which does not provide an information about the orientation of catheter tip 16 relative to the striped or marked portion of the catheter outside the body. In FIG. 8, assuming a clockwise (i.e., 12 to 3 o'clock) insertion was used, twisted stripe 24 indicates that the blockage is most likely right, or the tip is left of 12 o'clock. Similarly, in a counterclockwise insertion (i.e., 12 to 9 o'clock) a stripe twist which is the reverse of the twist of FIG. 8 would also indicate that the tip is blocked to the right of 12 o'clock. The operator, armed with this information, will now be able to determine which way to make a quarter turn of the catheter to try to get around the obstruction, placing the longitudinal holes 20 and 22 in the position least likely to cause tissue damage.

Figure 9:
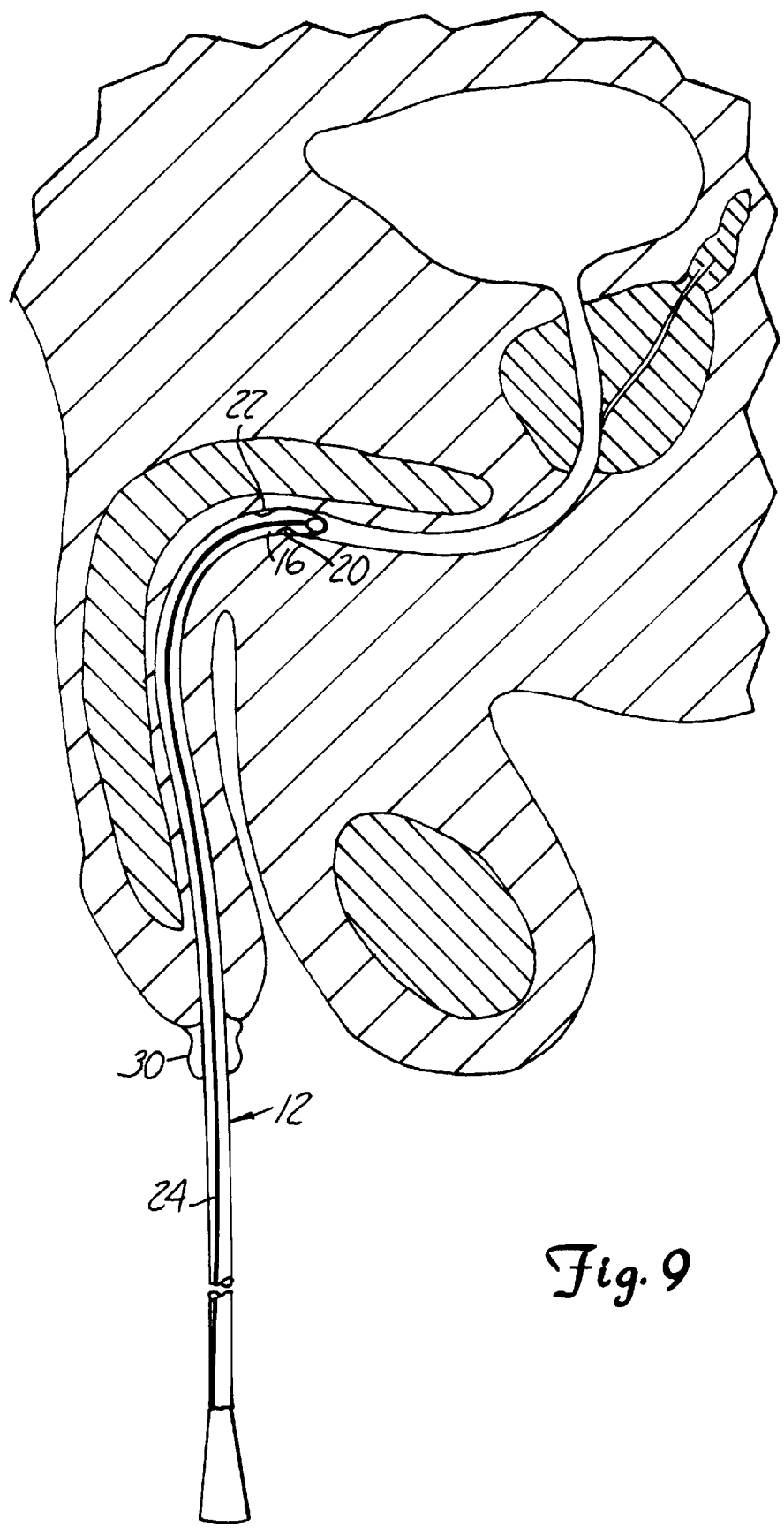
FIG. 9 illustrates a side view of an obstructed insertion.

The pattern of twisted stripe 24, shown in FIG. 9, indicates a right blockage assuming the hand of the operator is in the 12 o'clock position. If the operator makes a reverse one-quarter twist and the catheter does not straighten out as shown in FIG. 7, indicated by stripe 24 being straight as shown in FIG. 7, then the operator has learned that the catheter is either in a reduced diameter portion of the track or some type of growth or blockage is in a 12 o'clock position. If the operator pulls straight back slightly on the catheter, the stripe 24 straightens as shown in FIG. 7, the operator has now obtained some additional information to attempt to get through the reduced portion of the track or around the blockage. For example, the operator may try to insert slightly right and left of the previous twist, or remove the catheter and try a smaller size diameter catheter.

Figure 10:
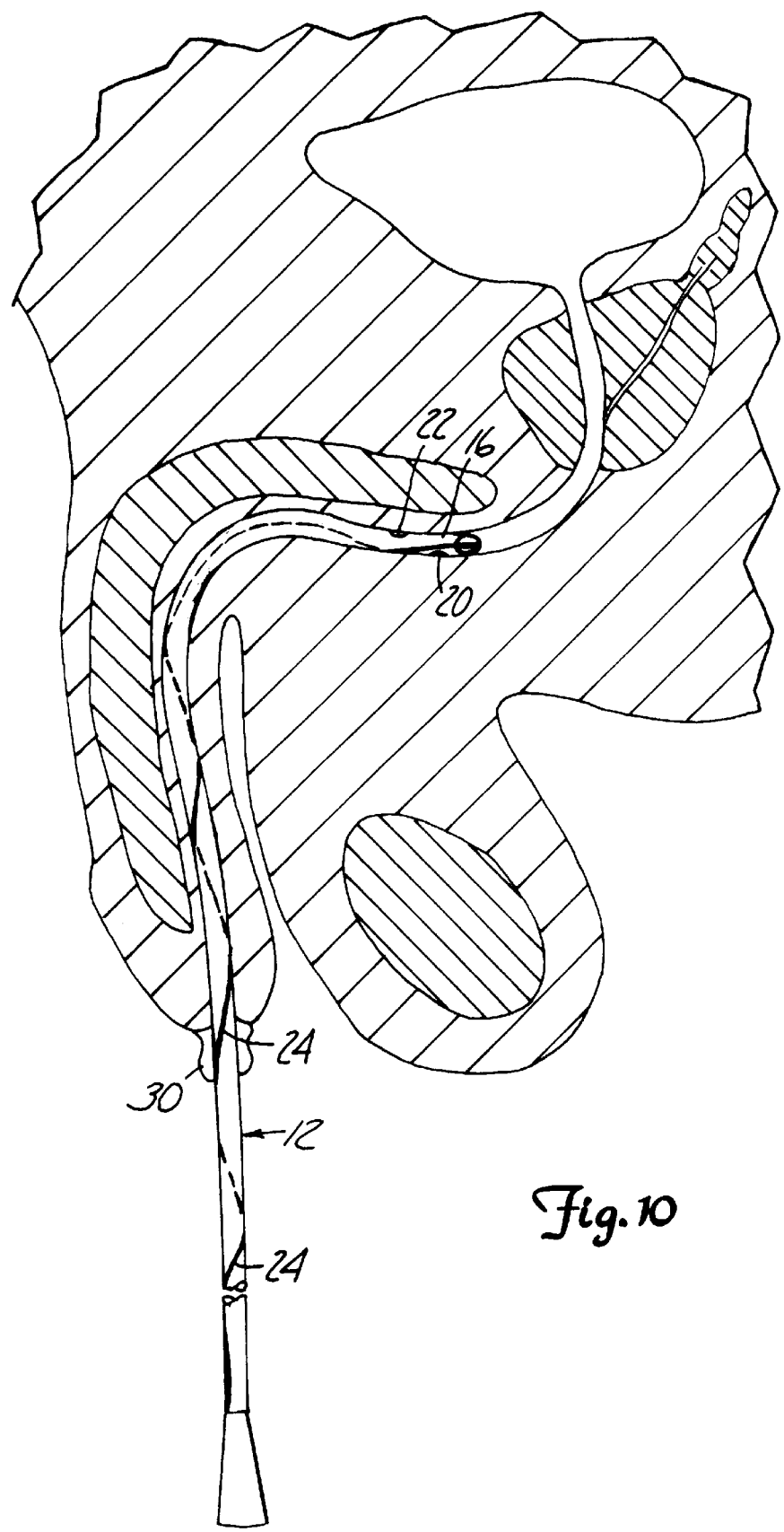
FIG. 10 illustrates a side view of an obstructed insertion.

Similarly, the twisted stripe 24 shown in FIG. 10 shows a left obstruction if the hand is in the 12 o'clock position. The operator may try the same techniques as discussed above in connection with FIG. 9 in order to learn where the obstruction is relative to the catheter tip 16, and to get around the blockage with the longitudinal holes 20 and 22 positioned to cause the least tissue damage.

The longitudinal stripe 24 tells the operator where the tip 16 is from outside the body without having to take an x-ray. With the stripe indicating where the tip 16 is, the operator now knows that the eyelets or holes are 90° and 270° relative to the tip 16.

Figure 11:
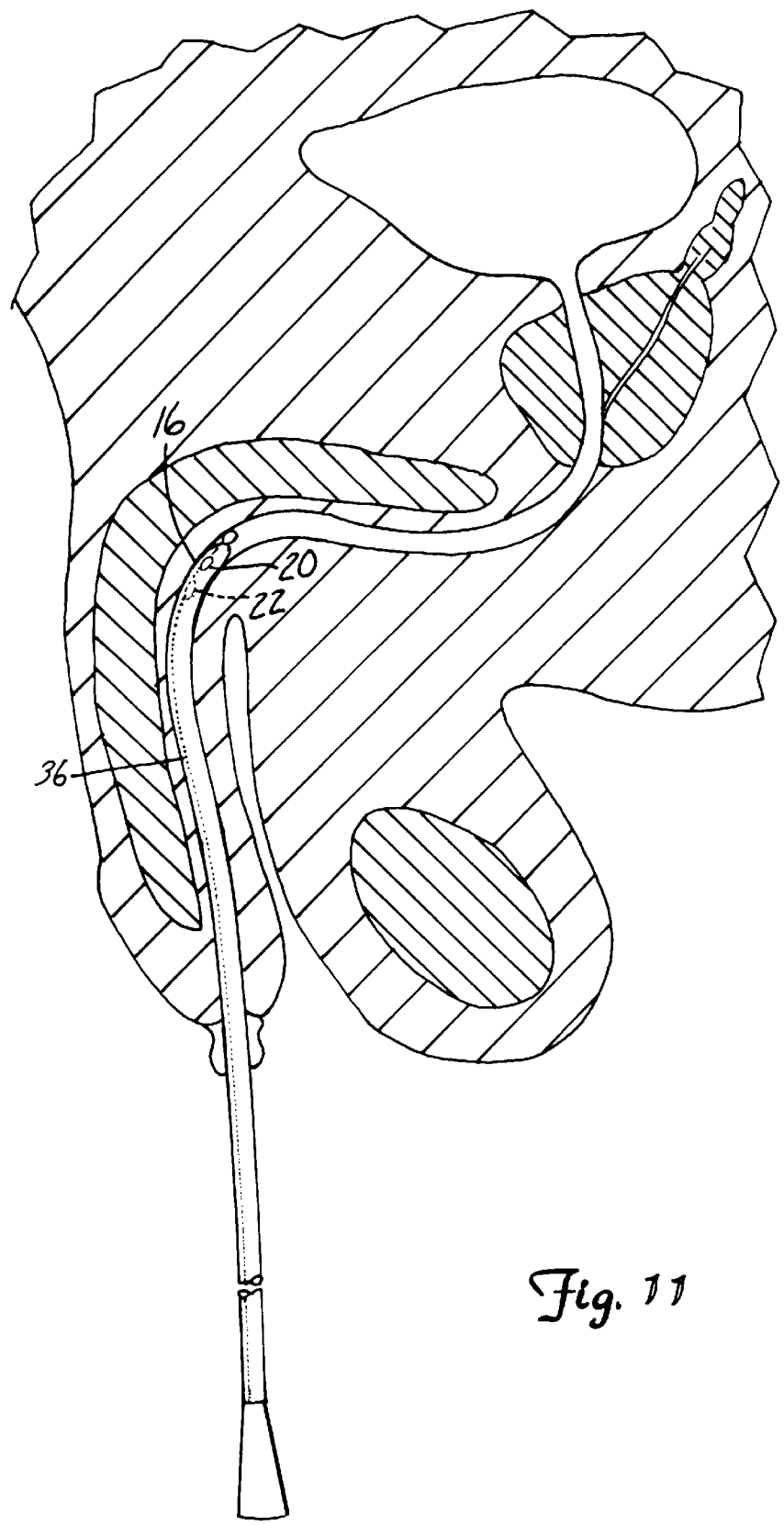
FIG. 11 illustrates a top view of the urinary catheter having a visible sequence of marks during an unobstructed insertion.

Referring now to FIGS. 11–14, an alternative embodiment of a urinary catheter is shown with an unobstructed insertion and in a variety of obstructed insertion situations, as seen in previous FIGS. 7–10. As in the previous figures, in the preferred embodiment, the longitudinal holes 20 and 22 are arranged at 3 and 9 o'clock relative to the catheter tip 16. Turning now to FIG. 11, the visual sequence of marks 36 allows the operator to know where the holes or eyelets 20 and 22 and the tip are relative to the portion of the catheter outside the body during the insertion process. In FIG. 11, the visible sequence of marks 36 are in the form of a sequence of dots arranged along a longitudinal axis of the catheter forming a substantially linear pattern along the catheter. Therefore, as in the previous embodiment, the operator is able to guide the curved tip of the catheter about the visible sequence of marks, changing the orientation of the longitudinal holes 20 and 22 and minimizing the amount of tissue damage, if the operator detects pressure upon catheter insertion against a blockage or an obstruction.

FIG. 11 shows a top view of the urinary catheter during an unobstructed insertion and shows that the visible sequence of marks or dots 36 form a straight line pattern. Visible sequence of marks 36 can, again, be any desired color, so long as the color is readily apparent to the operator. The colors blue or black provide sufficient contrast to the color of the catheter known in the art to be clear or opaque-white, for example.

Figure 12:
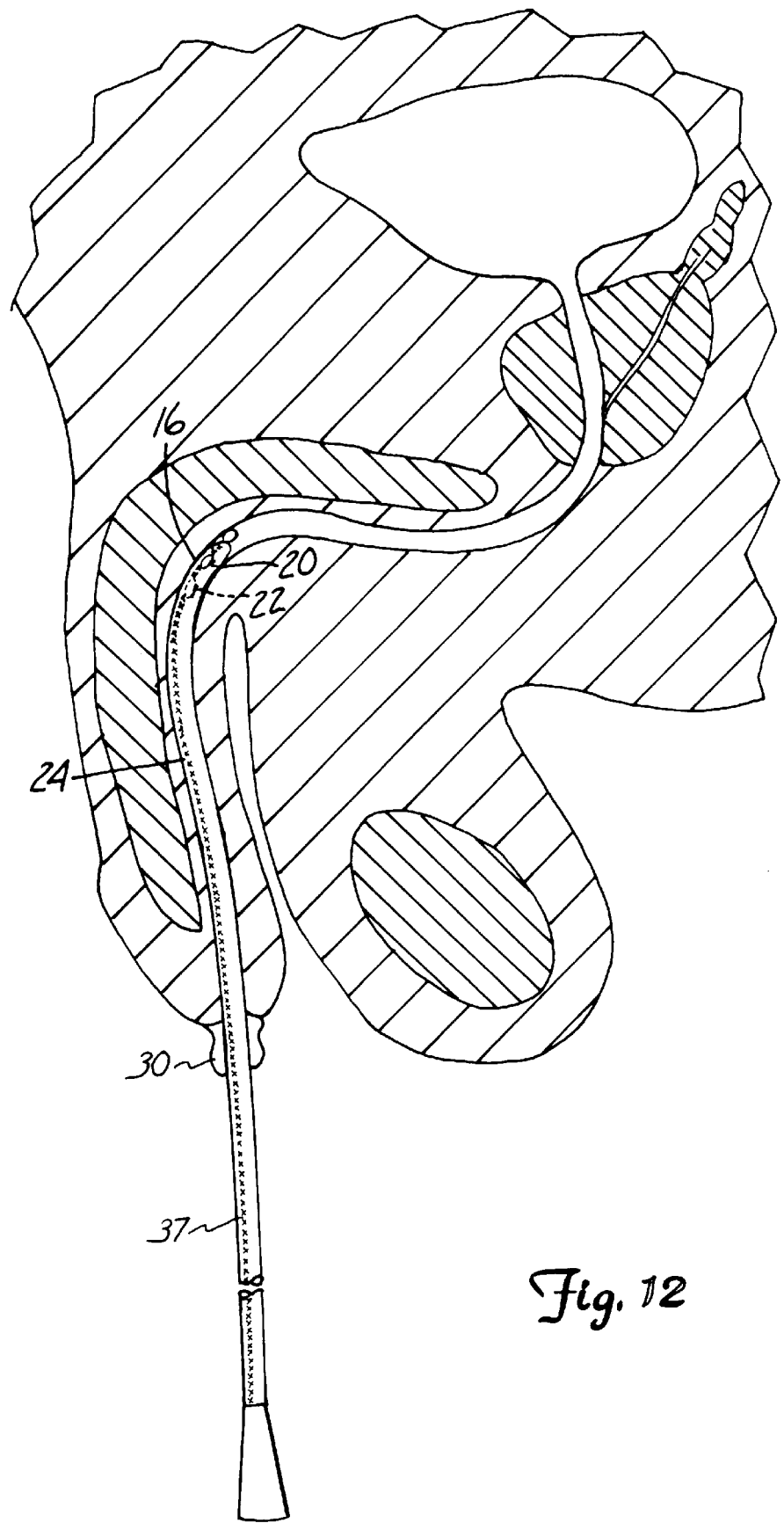
FIG. 12 illustrates a top view of an obstructed insertion showing the visible sequence of marks twisted.

FIG. 12 shows a catheter 10 with the visible marks 36 twisted. As hereinbefore stated, if the catheters encounters a growth, obstruction or other blockage in the urinary track, the greater frictional force exerted on the tip 16 will prevent the entire axial length of the tube 12 from rotating simultaneously, causing the twising of the visible sequence of marks 36. Again, the information provided by the positioning of the catheter is the same as that previously described. The visible sequence of marks can be utilized to the same extent as that described for FIGS. 8–10 above.

Figure 13:
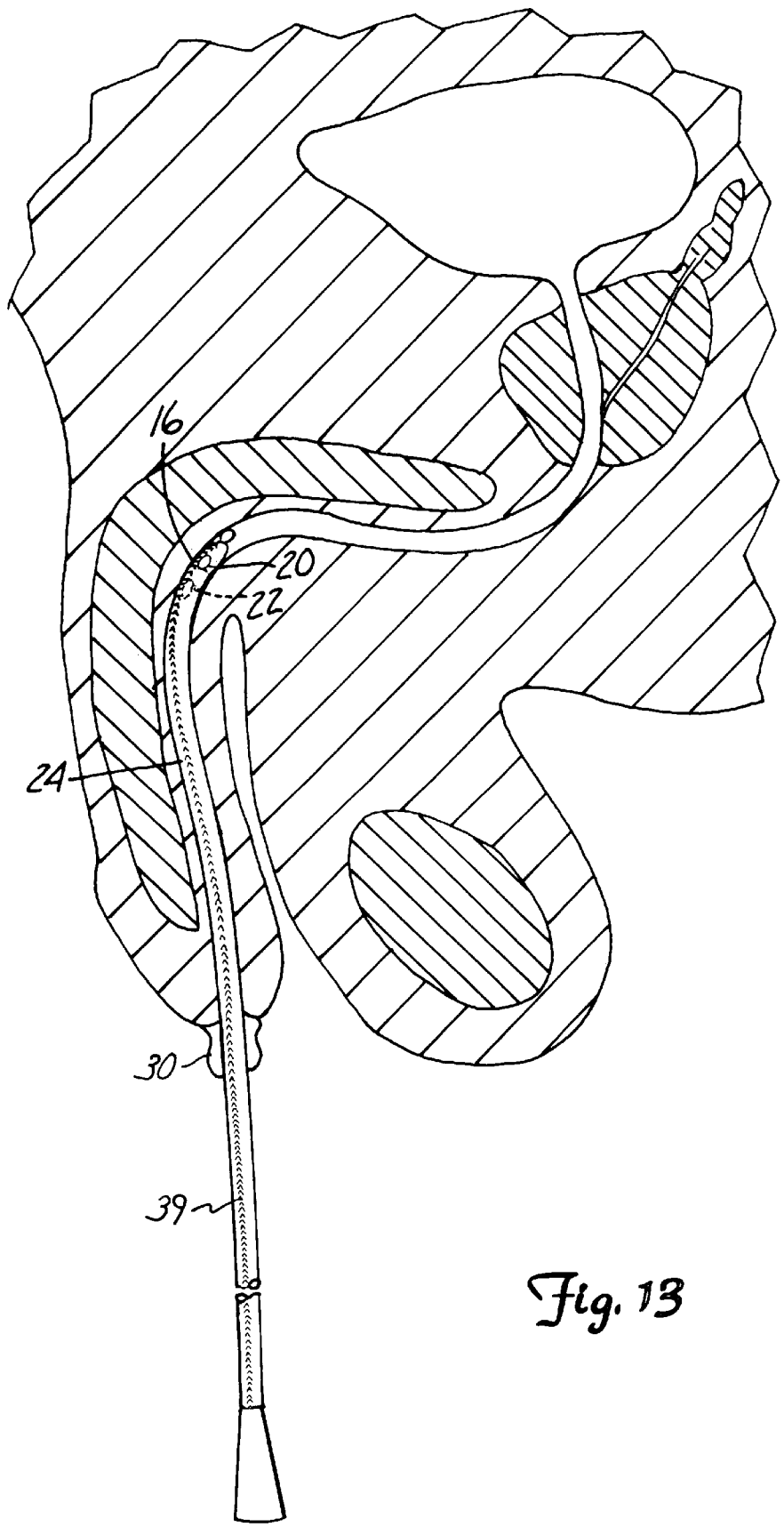
FIG. 13 illustrates an alternative embodiment of the visible sequence of marks in the present invention.

FIG. 13 shows an alternative embodiment of the visible sequence of marks of the present invention, showing the visible sequence of markings as the character "x" aligned to form a substantially straight line 37. Similarly, FIG. 14 shows yet another embodiment of the visible sequence of marks of the present invention, showing the visible sequence of markings as the character "v" aligned to form a substantially straight line 39.

It is to be understood that the visible sequence of marks 36 is situated in the same relationship with the curved tip 16 and longitudinal holes 20 and 22 as previously described for the visible stripe 24 in FIGS. 7–10. Further, the visible sequence of marks can be of a sequence of any appropriate symbol, such as dots, small circles, the character "x", arrows, etc., so long as the symbol chosen can be aligned in a substantially straight line along the length of the catheter.

Various modifications can be made to the present invention without departing from the apparent scope hereof.

I claim:

1. A catheter for catheterization of a tortuous body lumen comprising:
   a distal end;
   a proximal end;
   a tube extending between the distal and proximal ends and defining a longitudinal axis;
   a tip portion at the distal end of the catheter, the tip extending radially away from the longitudinal axis; and
   a visible marking formed on the tube, wherein the tube is susceptible to twisting about the longitudinal axis upon contact with an obstruction within the lumen, the visible marking being modulated according to the twisting and thereby providing an indication of the twisting and the relative position of the tip portion.

2. The catheter of claim 1, wherein said tube defines a hole on a side of the tube adjacent the tip portion.

3. The catheter of claim 1, wherein said visible marking comprises a sequence of marks that extend longitudinally along the tube.

4. The catheter of claim 1, wherein said visible marking comprises a stripe that extends longitudinally along the tube.

5. A urinary catheter for insertion by an operator into a tortuous body lumen past an obstruction, said urinary catheter comprising:
   a catheter tube having a longitudinal axis and a visible sequence of marks arranged generally parallel with said longitudinal axis of said catheter tube, said visible sequence of marks contrasting with said catheter tube so as to be readily apparent to the operator, said catheter tube having an insertion end and a manipulation end, said visible sequence of marks extending sufficiently toward said manipulation end of said catheter tube so as to be exposed outside the tortuous body lumen when said catheter tube is at least partially inserted within said tortuous body lumen; and
   a tip connected to said insertion end of said catheter tube and extending radially from said catheter tube at a predetermined angle relative to said longitudinal axis, said catheter tube further defining a hole extending at least partially through said catheter tube generally proximate to said tip, wherein said visible sequence of marks provides a visual indication to the operator of the relative positions of said tip and said hole from outside the tortuous body lumen once the tip is inserted into the tortuous body lumen, thus allowing the operator to manipulate said manipulation end of said catheter tube so as to position and orient said tip and said hole relative to the obstruction so as to cause a minimum of tissue damage when the catheter tube is moved past the obstruction, and wherein the catheter tube is fabricated from a longitudinally flexible biocompatible plastic material such that upon insertion into and removal from the tortuous body lumen rotation of the manipulation end of the catheter tube will simultaneously rotate the tip and the visible sequence of marks a substantially equal amount, but such that insertion into and removal from a portion of the tortuous body lumen containing the obstruction will cause the visible sequence of marks to twist when the manipulation end of the catheter tube is rotated, said twisting of the visible sequence of marks being visible to the operator along a portion of the catheter tube exposed outside the tortuous body lumen thereby enabling the operator to determine the position and orientation of the tip and hole relative to the manipulation end and the obstruction.

6. The urinary catheter of claim 5 wherein the hole is a first hole, said urinary catheter further comprising:
   a second hole extending at least partially through the catheter tube and disposed generally proximate to the tip, said second hole being located generally diametrically opposing the first hole, the visible sequence of marks enabling the operator to locate the position and orientation of the tip, the first hole, and said second hole during insertion and removal of the catheter tube from outside the tortuous body lumen such that tissue damage from said tip, the first hole, or said second hole is minimized.

7. The urinary catheter of claim 5 wherein the visible sequence of marks are generally aligned along the catheter tube in an arrangement forming a substantially linear pattern generally parallel with the longitudinal axis.

8. A catheter for insertion by an operator through a tortuous body lumen past an obstruction, said catheter comprising:
   a tube having an insertion end, a manipulation end, a side portion, and a longitudinal axis, said side portion having a sequence of visible indicia contrasting with said side portion so as to be readily apparent to the operator, said sequence of visible indicia extending sufficiently along said tube such that a portion of said sequence of visible indicia is exposed outside the tortuous body lumen when said tube is at least partially inserted within the tortuous body lumen, said tube being susceptible to twisting about said longitudinal axis upon contact with an obstruction, and said visible indicia being modulated according to the twisting and thereby providing an indication of the twisting; and
   a tip connected to and extending from said insertion end of said tube in a direction radially away from said longitudinal axis of said tube, said direction being at a predetermined angle relative to said sequence of visible indicia, said tube further defining a hole extending at least partially through said side portion and disposed generally proximate to said tip, said hole being positioned at a predetermined location relative to said tip and a predetermined angle relative to said sequence of visible indicia,
   whereby the portion of the sequence of visible indicia disposed outside the tortuous body lumen provides a visual indication of the relative positions of the tip and the hole from outside the tortuous body lumen such that the operator selectively manipulates the manipulation end of the tube to position and orient the tip and the hole of the urinary catheter such that movement of the tube past the obstruction will cause a minimum of tissue damage.

9. A urinary catheter for insertion by an operator through a tortuous body lumen past an obstruction, said urinary catheter comprising:
   a tube having an insertion end, a manipulation end, a side portion, and a longitudinal axis, said side portion having a visible stripe contrasting with said side portion so as to be readily apparent to the operator, said visible stripe extending sufficiently along said tube such that a portion of said visible stripe is exposed outside the tortuous body lumen when said tube is at least partially inserted within the tortuous body lumen; and
   a tip connected to and extending from said insertion end of said tube in a direction radially away from said longitudinal axis of said tube, said direction being at a predetermined angle relative to said visible stripe, said tube further defining a hole extending at least partially through said side portion and disposed generally proximate to said tip, said hole being positioned at a predetermined location relative to said tip and a predetermined angle relative to said visible stripe,
   whereby the portion of the visible stripe disposed outside the tortuous body lumen provides a visual indication of the relative positions of the tip and the hole from outside the tortuous body lumen such that the operator selectively manipulates the manipulation end of the tube to position and orient the tip and the hole of the urinary catheter such that movement of the tube past the obstruction will cause a minimum of tissue damage, said tube being susceptible to twisting about said longitudinal axis upon contact with an obstruction, and said visible stripe being modulated according to the twisting and thereby providing an indication of the twisting.

10. The urinary catheter of claim 9, wherein the visible stripe is co-extruded with the tube.

11. The urinary catheter of claim 9, wherein the visible stripe is printed on the side portion of the tube.

12. The urinary catheter of claim 9, wherein the visible stripe is marked on the side portion of the tube.

13. The urinary catheter of claim 9, wherein the tip is curved and tapered.

14. The urinary catheter of claim 9, wherein the tip is formed into a round member having a closed distal end.

15. A catheter for insertion by an operator into a tortuous body lumen past an obstruction, said catheter comprising:
   a tube having a substantially circular cross-section, said tube having an insertion end terminating in a curved tip and a second end, said tube having a side portion and a longitudinal axis, said curved tip connected to and extending radially from said insertion end of said tube at a predetermined angle relative to said longitudinal axis;
   a visible stripe contrasting with said side portion of said tube so as to be readily apparent to the operator, said visible stripe extending from said insertion end toward said second end of said tube such that a portion of said visible stripe is exposed outside the tortuous body lumen when said tube is at least partially inserted within said tortuous body lumen, said visible stripe being positioned at a predetermined position relative to said curved tip; and
   a hole defined by and extending at least partially through said side portion of said tube generally proximate to said curved tip, said hole being oriented a predetermined angle from said visible stripe,
   whereby the portion of the visible stripe exposed outside the tortuous body lumen enables the operator to locate the hole and the curved tip of the tube after insertion into the tortuous body lumen relative to the manipulation end of the tube, such that the operator selectively manipulates the position and orientation of the curved tip and the hole as the catheter passes the obstruction to cause a minimum of tissue damage, and wherein said tube is fabricated from a longitudinally flexible biocompatible plastic material such that upon insertion into and removal from the tortuous body lumen rotation of the manipulation end of the tube will simultaneously rotate the curved tip a substantially equal amount in the same direction, but such that insertion into and removal from a portion of the tortuous body lumen containing the obstruction will cause the visible stripe to twist when the manipulation end of the tube is rotated, the twisting of the visible stripe being visible to the operator from outside the tortuous body lumen, thereby enabling the operator to determine the orientation of the curved tip and the hole relative to the manipulation end.

16. The catheter of claim 15, wherein the catheter is a urological catheter.

17. The catheter of claim 16, wherein the hole is a first hole, said catheter further comprising:

a second hole extending at least partially through the side portion of the tube and disposed generally proximate to the curved tip, said second hole being located generally diametrically opposing the first hole, the visible stripe enabling the operator to locate the curved tip, the first hole, and the second hole during insertion and removal of the catheter from the tortuous body lumen such that tissue damage is minimized.

18. A method for inserting a catheter into a tortuous body lumen, the method comprising:

a) providing the catheter, the catheter comprising:
   a distal end;
   a proximal end;
   a tube extending between the distal and proximal ends and defining a longitudinal axis;
   a tip portion at the distal end of the catheter, the tip extending radially away from the longitudinal axis; and
   a visible marking formed on the tube, wherein the tube is susceptible to twisting about the longitudinal axis upon contact with an obstruction within the lumen, the visible marking being modulated according to the twisting and thereby providing an indication of the twisting;

b) inserting the distal end of the catheter into the tortuous body lumen;

c) ascertaining the orientation of the tip portion based on the modulation of the visible marking; and d) manipulating a portion of the catheter that is outside the tortuous body lumen based on the modulation of the visible marking to orient the tip portion such that tissue damage is minimized during movement of the catheter.

19. The method of claim 18, wherein the tube defines a hole on a side of the tube adjacent the tip portion.

20. The method of claim 19, wherein the method further comprises manipulating a portion of the catheter that is outside the tortuous body lumen based on the modulation of the visible marking to orient the hole such that tissue damage is minimized during movement of the catheter.

21. The method of claim 18, wherein the tortuous body lumen contains an obstruction.

22. The method of claim 21, wherein the method further comprises manipulating a portion of the catheter that is outside the tortuous body lumen based on the modulation of the visible marking to orient the tip portion such that movement of the distal end past the obstruction causes minimal tissue damage.

23. A method for an operator to insert a catheter into a tortuous body lumen containing an obstruction, said catheter having an upper portion, a lower portion, a manipulation end, an insertion end, and a side portion, said insertion end terminating in a tip extending generally away from said upper portion, said catheter defining a hole disposed along said side portion of said catheter generally proximate to said tip, said method comprising the steps of:

providing the catheter with a visible stripe contrasting with the side portion of the catheter so as to be readily apparent to the operator, said visible stripe disposed on and extending longitudinally along the catheter such that a portion of said visible stripe is exposed and visible outside the tortuous body lumen when the catheter is at least partially inserted within the tortuous body lumen;

inserting the insertion end of the catheter into the tortuous body lumen;

observing said portion of said visible stripe on the catheter disposed outside the tortuous body lumen to determine based upon that observation whether the insertion end of the catheter has encountered the obstruction; and manipulating the catheter to position the tip and the hole relative to the obstruction so that movement of the catheter past the obstruction will cause the least amount of tissue damage.

24. The method of claim 23 wherein the obstruction is a tissue body and the step of manipulating the catheter is accomplished so as to cause the least amount of tissue damage to the obstruction by the hole.

25. The method of claim 23 wherein the step of manipulating the catheter is accomplished so as to cause the least amount of tissue damage to the tortuous body lumen by the hole.

26. The method of claim 23 wherein the obstruction is a tissue body and the step of manipulating the catheter is accomplished so as to cause the least amount of tissue damage to the obstruction by the tip of the catheter tube.

27. The method of claim 23 wherein the step of manipulating the catheter is accomplished so as to cause the least amount of tissue damage to the tortuous body lumen by the tip of the catheter tube.

28. The method of claim 23 wherein the tip of the catheter extends radially from the insertion end of the catheter at a predetermined angle relative to the longitudinal axis of the catheter tube.

29. The method of claim 28 wherein the tip of the catheter tube forms a curve relative to the catheter tube.

30. A method for an operator to insert a catheter into a tortuous body lumen containing an obstruction, said catheter having an upper portion, a lower portion, a manipulation end, an insertion end, and a side portion, said insertion end terminating in a tip extending generally away from said upper portion, said catheter defining a hole disposed along said side portion of said catheter generally proximate to said tip, said method comprising the steps of:

providing the catheter with a sequence of visible indicia contrasting with the side portion of the catheter so as to be readily apparent to the operator, said sequence of visible indicia disposed on and extending longitudinally along the catheter such that a portion of said sequence of visible indicia is exposed and visible outside the tortuous body lumen when the catheter is at least partially inserted within the tortuous body lumen;

inserting the insertion end of the catheter into the tortuous body lumen;

observing said portion of said sequence of visible indicia on the catheter disposed outside the tortuous body lumen to determine based upon that observation whether the insertion end of the catheter has encountered the obstruction; and manipulating the catheter to position the hole relative to the obstruction so that movement of the catheter past the obstruction will cause the least amount of tissue damage.

31. The method of claim 30 wherein the obstruction is a tissue body and the step of manipulating the catheter is accomplished so as to cause the least amount of tissue damage to the obstruction by the hole.

32. The method of claim 30 wherein the step of manipulating the catheter is accomplished so as to cause the least amount of tissue damage to the tortuous body lumen by the hole.

33. The method of claim 30 wherein the obstruction is a tissue body and the step of manipulating the catheter is accomplished so as to cause the least amount of tissue damage to the obstruction by the tip of the catheter tube.

34. The method of claim 30 wherein the step of manipulating the catheter is accomplished so as to cause the least amount of tissue damage to the tortuous body lumen by the tip of the catheter tube.

35. The method of claim 30 wherein the tip of the catheter extends radially from the insertion end of the catheter at a predetermined angle relative to the longitudinal axis of the catheter tube.

36. The method of claim 35 wherein the tip of the catheter tube forms a curve relative to the catheter tube.

37. A method for an operator to insert a catheter into a tortuous body lumen containing an obstruction, said method comprising the steps of:

providing a catheter tube having a substantially circular cross-section, said catheter tube having a manipulation end and an insertion end, said catheter tube having an upper portion, a lower portion, and a side portion, said insertion end terminating in a curved tip extending generally away from said lower portion, said catheter tube further having a visible stripe of contrasting color so as to be readily apparent to the operator, said visible stripe disposed on and extending longitudinally along said upper portion of said catheter tube such that a portion of said visible stripe is exposed and visible outside the tortuous body lumen when said catheter tube is at least partially inserted within the tortuous body lumen, said catheter tube defining a hole extending at least partially through said side portion of said catheter tube and disposed generally proximate to said curved tip;

inserting said insertion end of said catheter tube into the tortuous body lumen;

observing said visible stripe at a location on said catheter tube disposed outside the tortuous body lumen to determine based upon that observation of said visible stripe whether said insertion end of said catheter tube has encountered the obstruction; and manipulating said catheter tube to position said hole relative to the obstruction so that movement of said catheter tube past the obstruction will cause the least amount of tissue damage.

* * * * *